(12) United States Patent
Gross et al.

(10) Patent No.: US 11,077,161 B2
(45) Date of Patent: Aug. 3, 2021

(54) NATURAL ANTI-INFLAMMATORNY COMPOSITIONS AND METHODS OF USE

(71) Applicant: Orthopedic Solutions LLC, Blue Bell, PA (US)

(72) Inventors: Michael B. Gross, Plymouth Meeting, PA (US); Javad Parvizi, Gladwyne, PA (US)

(73) Assignee: Orthopedic Solutions LLC, Blue Bell, PA (US)

( * ) Notice: Subject to any disclaimer, the term of this patent is extended or adjusted under 35 U.S.C. 154(b) by 0 days.

(21) Appl. No.: 16/690,317

(22) PCT Filed: Mar. 16, 2018

(86) PCT No.: PCT/US2018/022947
§ 371 (c)(1),
(2) Date: Nov. 21, 2019

(87) PCT Pub. No.: WO2018/200095
PCT Pub. Date: Nov. 1, 2018

(65) Prior Publication Data
US 2020/0138897 A1    May 7, 2020

Related U.S. Application Data

(60) Provisional application No. 62/490,206, filed on Apr. 26, 2017.

(51) Int. Cl.
| | | |
|---|---|---|
| *A61K 36/00* | (2006.01) | |
| *A61K 36/9068* | (2006.01) | |
| *A61P 19/10* | (2006.01) | |
| *A61K 9/00* | (2006.01) | |
| *A61K 31/375* | (2006.01) | |
| *A61K 31/593* | (2006.01) | |
| *A61K 31/7048* | (2006.01) | |
| *A61K 36/324* | (2006.01) | |
| *A61K 36/9066* | (2006.01) | |
| *A61K 45/06* | (2006.01) | |

(52) U.S. Cl.
CPC ........ *A61K 36/9068* (2013.01); *A61K 9/0053* (2013.01); *A61K 31/375* (2013.01); *A61K 31/593* (2013.01); *A61K 31/7048* (2013.01); *A61K 36/324* (2013.01); *A61K 36/9066* (2013.01); *A61P 19/10* (2018.01); *A61K 45/06* (2013.01)

(58) Field of Classification Search
CPC ...................................................... A61K 36/00
USPC ......................................................... 424/725
See application file for complete search history.

(56) References Cited

U.S. PATENT DOCUMENTS 8,193,376 B2 *   6/2012   Gupta ...................... A61K 8/49
                                                      549/348
2003/0185907 A1   10/2003   Krumhar

FOREIGN PATENT DOCUMENTS

WO          2010054125 A1      4/2010

OTHER PUBLICATIONS

Sengupta, et al., "Comparative Efficacy and Tolerability of 5-Loxin and Aflapin Against Osteoarthritis of the Knee: A Double Blind, Randomized, Placebo Controlled Clinical Study," International Journal of Medical Sciences, 2010.
Block, "Boswellia Synergy Combats Osteoarthritis," Aug. 4, 2014; www.life-enhancement.com/magazine/article/2551-boswellia-synergy-combats-osteoarthritis.
Dragos et al."Phytomedicine in Joint Disorders," Nutrients, Jan. 16, 2017, 1-18.
International Search Report and Written Opinion dated Jun. 11, 2018 in PCT/US18/22947.

* cited by examiner

*Primary Examiner* — Michael V Meller
(74) *Attorney, Agent, or Firm* — White and Williams LLP

(57) ABSTRACT

This invention relates to methods for administering an effective amount of a dietary or nutritional supplement composition that effectively changes the levels of biomarkers in the synovium of a joint and resulting in decreased pain and ultimately better outcomes for subjects. The formulation comprises an effective amount of the following: *Boswellia*; Vitamin C; Ginger; Turmeric; Vitamin D3; and Rutin. In a preferred embodiment of the composition of the invention, the composition is substantially free of omega-3 fatty acids.

1 Claim, 4 Drawing Sheets

Figure 1: Flow chart of the patients who participated in the study.
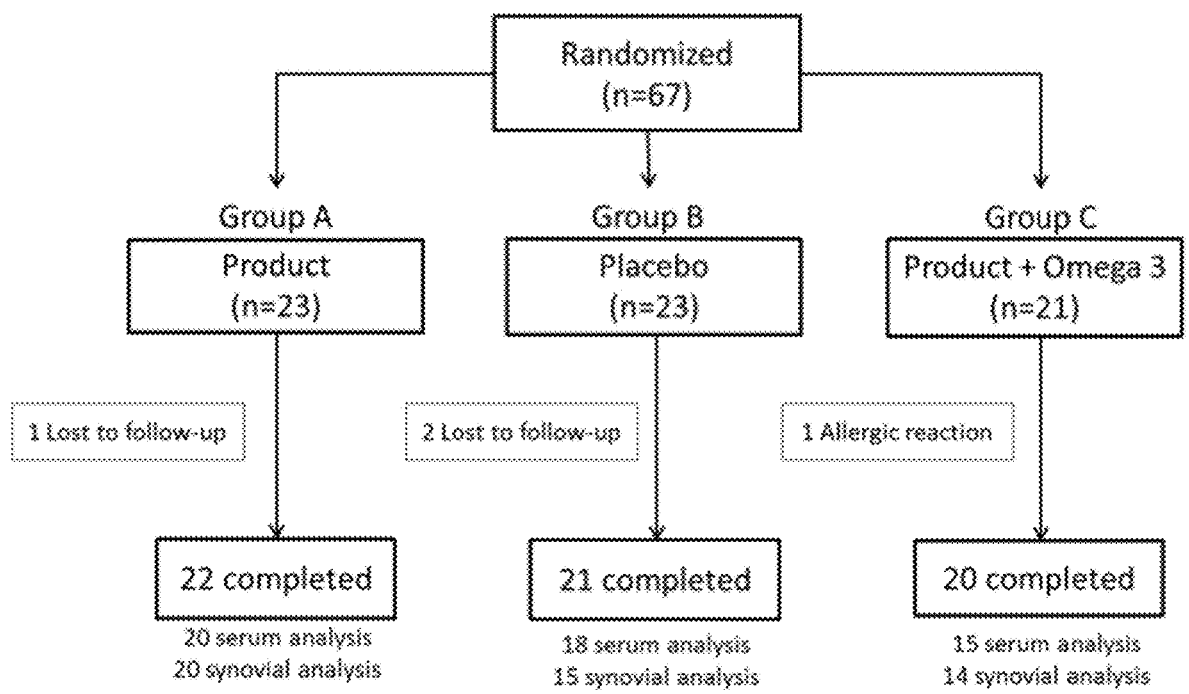

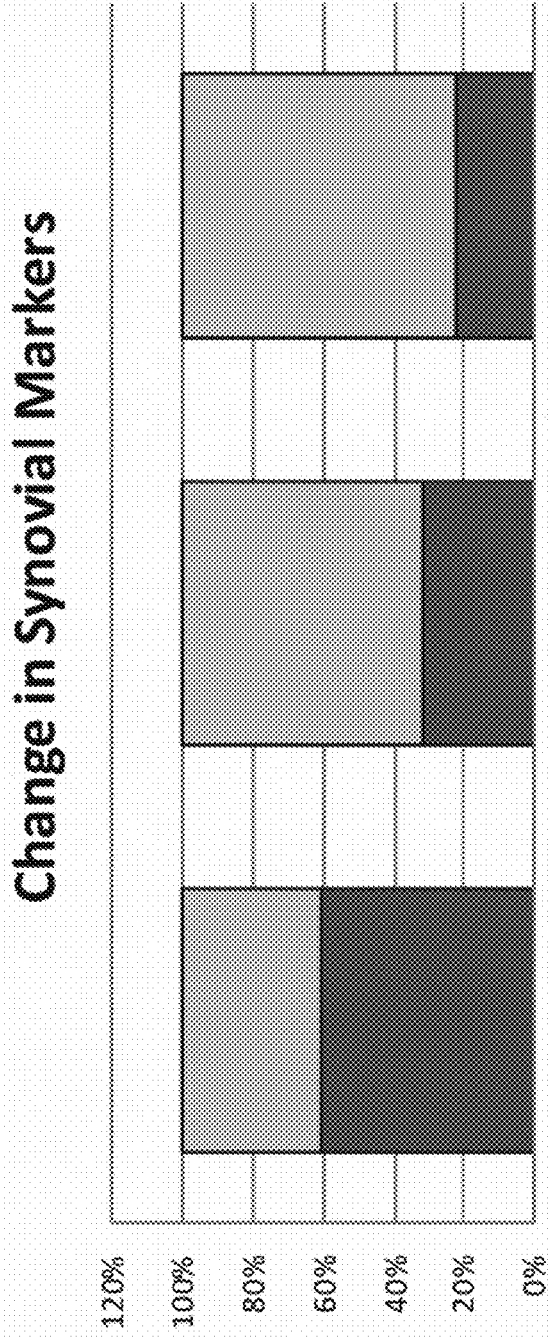
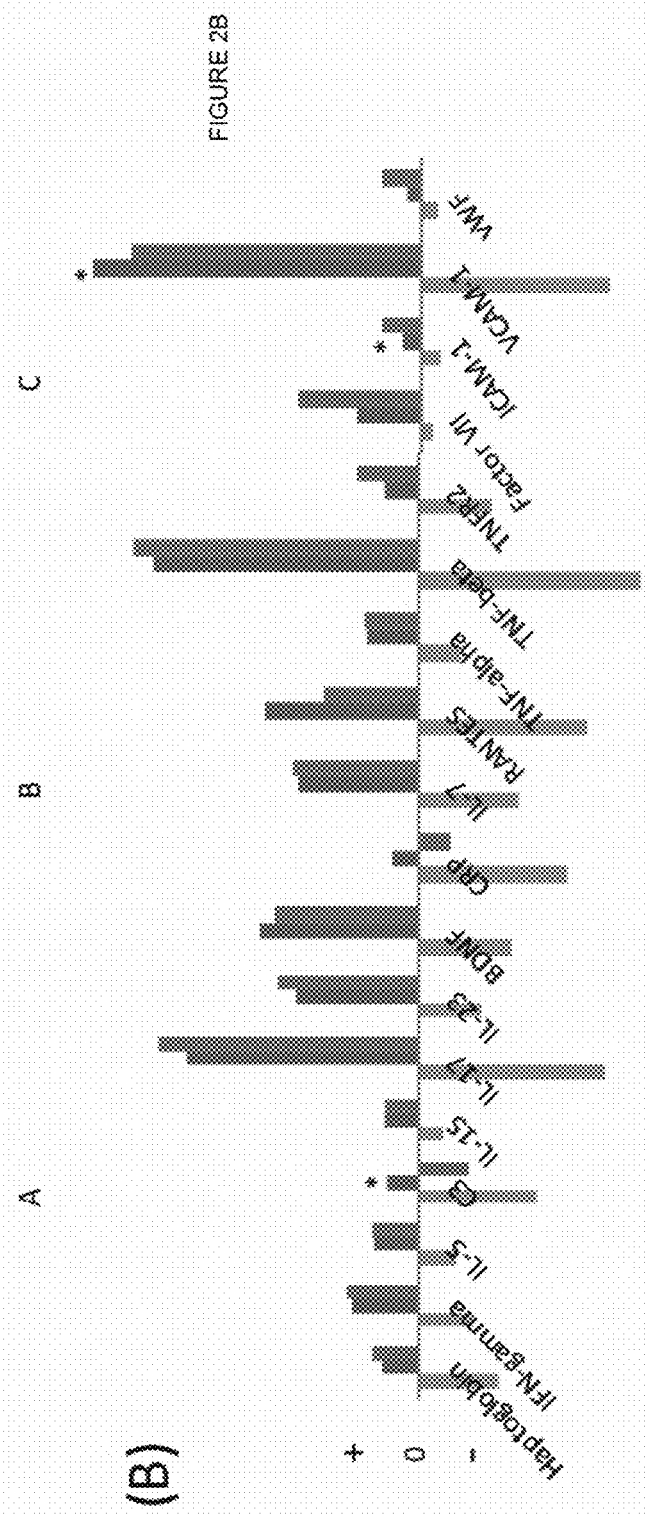

FIGURE 3
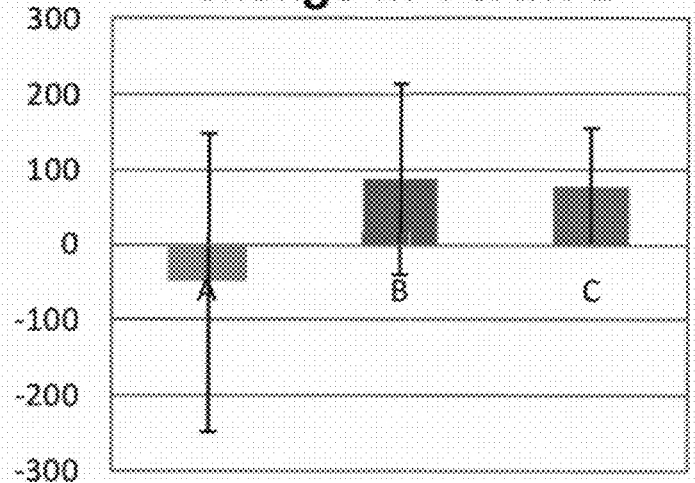
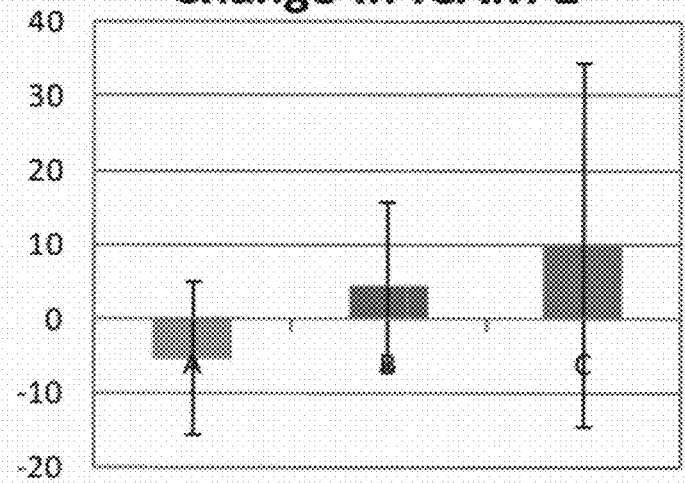
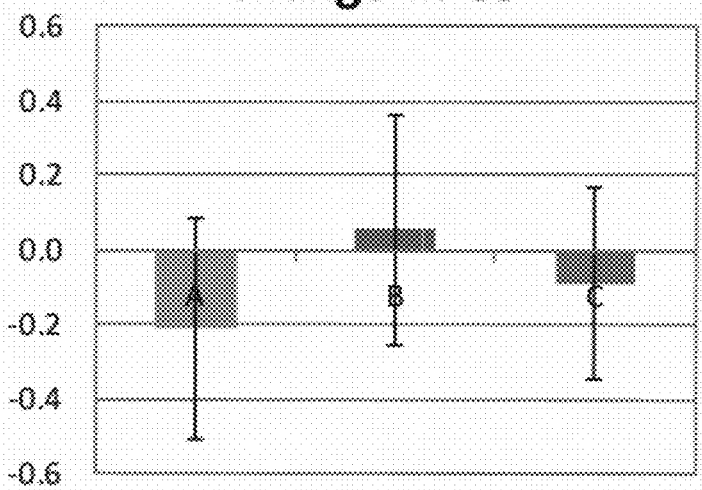

NATURAL ANTI-INFLAMMATORNY COMPOSITIONS AND METHODS OF USE

BACKGROUND OF THE INVENTION

Emerging evidence has shown that OA is caused by dysfunction of the immune system that leads to chronic inflammation. Individuals with OA have elevated levels of inflammatory markers such as nuclear factor kappa beta (NF-κB), interleukin-1 alpha (IL-1a). IL-6, IL-17, tumor necrosis factor (TNF)-α, as well as many others. Administration of anti-inflammatory drugs such as NSAIDs, through inhibition of prostaglandin-E2, does result in a reduction in the level of select group of inflammatory mediators while resulting in overexpression of others, leading to a relative metabolic imbalance.

Symptomatic knee osteoarthritis (OA) affects 6% of the adult population and occurs in 10% of those over age 60. Arthritis is a chronic condition that causes pain and functional limitation for the patient. The condition is progressive that results in the demise of the articular cartilage and leads to end stage arthritis of the knee and need for total knee arthroplasty (TKA) in many patients.

Although TKA is a relatively successful surgical procedure, it is only reserved for patients with end-stage arthritis of the knee. Patients with symptomatic mild or moderate arthritis of the knee may be managed by a variety of non-operative treatment strategies. These include physical therapy, weight loss, activity modification, administration of non-steroidal anti-inflammatory medications (NSAIDs), oral supplements (glucosamine, etc.), intra-articular injection of corticosteroids and/or viscosupplementation plus others. Most of these measures are believed to carry a relative degree of success in alleviating symptoms and improving function. However, administration of NSAIDs and intra-articular injection with corticosteroids carry potential adverse effects and may not be tolerated by some patients. In a recent meta-analysis all classes of NSAIDs were shown to result in cardiotoxicity as well as gastrointestinal side effects if used for a long period of time. Another recent study has implicated the frequent use of NSAIDs as a cause of decreasing male fertility.

Despite the availability of some non-operative strategies for management of symptomatic arthritis in general and for the knee in particular, the clinical scenario of patients with arthritis of the knee who have failed all the aforementioned non-operative treatment measures and continued to be symptomatic is not uncommon. The patients either do not respond to these treatment measures or are unable to tolerate them due to adverse events.

In recent years, attention has been given to potent natural products that are known to have anti-inflammatory properties. Numerous agents have been evaluated for reducing pain and improving function in arthritic patients and have had some success. While the mechanism of action of these products in relieving osteoarthritis is not completely understood, in-vitro studies indicate they have a role in reducing pro-inflammatory markers and mediators associated with cartilage damage.

The hypothesis of this randomized, prospective and blinded study was that oral administration of naturally occurring anti-inflammatory products, in combination, will result in a reduction of the inflammatory mediators in the knee joint and serum of patients with moderate arthritis of the knee.

SUMMARY AND OBJECT OF THE INVENTION

It will be readily understood that the components of the present invention, as generally described herein, could be modified, arranged and designed in a wide variety of different formulas. Thus, the following more detailed description of the embodiments of the composition and systems and methods of the present invention is not intended to limit the scope of the invention. The scope of the invention is as broad as claimed herein.

As used herein, the term "effective amount" includes the amount of *Boswellia*, Vitamin C, Ginger, Turmeric, Vitamin D3 and Rutin ("active ingredients") which are capable of either effectively changing the level of certain biomarkers in the synovium and/or reducing pain in a joint, specifically the knee, or preferably both of the foregoing.

The present invention provides for methods for treating inflammation and/or reducing pain in subjects with osteoarthritis by way of administering a nutritional or dietary supplement composition comprising an effective amount of *Boswellia*, Vitamin C, Ginger, Turmeric, Vitamin D3 and Rutin. In one embodiment, the supplementation may include an effective amount of *Boswellia*, Vitamin C, Ginger, Turmeric, Vitamin D3 and Rutin, in approximately a 2:20:5:8:12:2 ratio by weight. In a preferred embodiment, the formulation comprises *Boswellia* 100 mg; Vitamin C 1000 mg; Ginger 250 mg; Turmeric 400 mg; Vitamin D3 600 IU and Rutin 100 mg. In an even more preferred embodiment the formulation is substantially free of omega-3 fatty acids.

The invention also comprises methods of alleviating or reducing pain in a subject by administering to said subject the above mentioned formulation. In one embodiment, the aforementioned formulation is taken by the subject at least once a day. In a further embodiment, the aforementioned formulation of the invention is taken at least twice a day. In yet a further embodiment, the aforementioned formulation of the invention is taken at least three times a day. In a most preferred embodiment, the formulation of the invention is taken at least four times a day.

In another aspect, the invention comprises a method of reducing pain in a subject with osteoarthritis in a joint by administering to the subject a composition that modulates the level of a molecule present in the synovial fluid of said joint, wherein the molecule is selected from the group consisting of: Alpha-1-Antitrypsin (AAT); Alpha-2-Macroglobulin (A2Macro); Beta-2-Microglobulin (B2M); Brain-Derived Neurotrophic Factor (BDNF); C-Reactive Protein (CRP); Eotaxin-1; Factor VII; Ferritin (FRTN); Fibrinogen; Granulocyte-Macrophage Colony-Stimulat Factor (GM-CSF); Haptoglobin; Intercellular Adhesion Molecule 1 (ICAM-1); Interferon gamma (IFN-gamma); Interleukin-1 alpha (IL-1 alpha); Interleukin-1 beta (IL-1 beta); Interleukin-1 receptor antagonist (IL-1ra); Interleukin-2 (IL-2); Interleukin-3 (IL-3); Interleukin-4 (IL-4); Interleukin-5 (IL-5); Interleukin-6 (IL-6); Interleukin-7 (IL-7); Interleukin-8 (IL-8); Interleukin-10 (IL-10); Interleukin-12 Subunit p40 (IL-12p40); Interleukin-12 Subunit p70 (IL-12p70); Interleukin-15 (IL-15); Interleukin-17 (IL-17); Interleukin-18 (IL-18); Interleukin-23 (IL-23); Macrophage Inflammatory Protein-1 alpha (MIP-1 alpha); Macrophage Inflammatory Protein-1 beta (MIP-1 beta); Matrix Metalloproteinase-3 (MMP-3); Matrix Metalloproteinase-9 (MMP-9); Monocyte Chemotactic Protein 1 (MCP-1); Stem Cell Factor (SCF); T-Cell-Specific Protein RANTES (RANTES); Tissue inhibitor of Metalloproteinases 1 (TIMP-1); Tumor Necrosis Factor alpha (TNF-alpha); Tumor Necrosis Factor beta (TNF-beta); Tumor necrosis factor receptor 2 (TNFR2); Vascular Cell Adhesion Molecule-1 (VCAM-1); Vascular Endothelial Growth Factor (VEGF); Vitamin D-Bind Protein (VDBP); von Willebrand Factor (vWF); and Complement C3 (C3).

In a preferred embodiment, the molecule that is modulated in the synovium is selected from the group consisting of: Brain-Derived Neurotrophic Factor (BDNF); C-Reactive Protein (CRP); Factor VII; Haptoglobin; Intercellular Adhesion Molecule 1 (ICAM-1); Interferon gamma (IFN-gamma); Interleukin-3 (IL-3); Interleukin-15 (IL-15); Interleukin-17 (IL-17); Interleukin-23 (IL-23); T-Cell-Specific Protein RANTES (RANTES); Tumor Necrosis Factor alpha (TNF-alpha); Tumor Necrosis Factor beta (TNF-beta); Tumor necrosis factor receptor 2 (TNFR2); Vascular Cell Adhesion Molecule-1 (VCAM-1); von Willebrand Factor (vWF); Complement C3 (C3). In a further preferred embodiment, the selected molecule of the aforementioned method(s) is not modulated in the serum. In a further embodiment, the levels of the modulated molecules are decreased in the synovium of subjects with osteoarthritis after administration of the composition of the invention, when compared to the levels of said molecules prior to administration. In an even more preferred embodiment, the pharmaceutical composition reduces the level of VCAM-1 and ICAM-1 in the synovial fluid of said joint. In a most preferred embodiment the composition does not substantially modulate the levels of VCAM-1 or ICAM-1 in the serum of a subject that has been administered the composition of the invention.

The invention further encompasses a formulation consisting of the following: Boswellia 100 mg; Vitamin C 1000 mg; Ginger 250 mg; Turmeric 400 mg; Vitamin D3 600 IU and Rutin 100 mg either in a unit dose or multiple dosage formulation(s). In a preferred embodiment, said formulation is substantially free of omega-3 fatty acids.

It should be noted that the novel formulations of the invention can be delivered in any form but are preferably formulated to be delivered orally. In a preferred embodiment the formulation of the embodiment is taken orally four times a day.

In a further embodiment, the formulation(s) of the invention are administered to subjects with osteoarthritis to reduce pain and improve functioning. In a preferred embodiment, the subjects suffer from osteoarthritis of the knee.

In a further aspect, the invention comprises a method of reducing the levels of VCAM-1 and ICAM-1 in the synovial fluid of the joint of a subject by administering a natural formulation. In one embodiment the natural formulation comprises an effective amount of Boswellia, Vitamin C, Ginger, Turmeric, Vitamin D3 and Rutin. In a further embodiment, the subject suffers from osteoarthritis. In a preferred embodiment, synovial levels of VCAM-1 and ICAM-1 are significantly reduced. In yet a further preferred embodiment, synovial levels of VCAM-1 and ICAM-1 and C3 are significantly reduced in subjects after administration of the composition of the invention.

In a further aspect of the invention a subject that is receiving the natural formulation of the invention is not also concurrently receiving either NSAIDS. IN another aspect, the subject is not receiving omega-3 fatty acids. In another embodiment the subject is receiving neither NSAIDs nor omega-3 fatty acids concurrently with the formulation of the invention.

It should be noted that the above detailed description of the invention should not be deemed as limiting ad the invention is more fully described by the examples below.

DETAILED DESCRIPTION

It will be readily understood that the components of the present invention, as generally described herein, could be modified, arranged and designed in a wide variety of different formulas. Thus, the following more detailed description of the embodiments of the composition and systems and methods of the present invention is not intended to limit the scope of the invention. The scope of the invention is as broad as claimed herein.

As used herein, the term "effective amount" includes the amount of Boswellia, Vitamin C, Ginger, Turmeric, Vitamin D3 and Rutin ("active ingredients") which are capable of effectively changing the level of certain biomarkers in the synovium and/or reducing pain in a joint, specifically the knee. Preferably the "effective amount" of the formulation of the invention both changes the level of certain biomarkers in the synovium and reduces pain in the joint of a subject with joint pain.

The present invention provides for methods for treating inflammation and/or reducing pain in Osteoarthritis by way of administering a nutritional or dietary supplement composition comprising an effective amount of Boswellia, Vitamin C, Ginger, Turmeric, Vitamin D3 and Rutin. In one embodiment, the supplementation may include an effective amount of Boswellia, Vitamin C, Ginger, Turmeric, Vitamin D3 and Rutin in approximately a 2:20:5:8:12:2 ratio by weight. Specifically, a formulation comprising Boswellia 100 mg; Vitamin C 1000 mg; Ginger 250 mg; Turmeric 400 mg; Vitamin D3 600 IU and Rutin 100 mg was found to be effective.

In one embodiment, the aforementioned formulation is taken by the subject at least once a day. In a further embodiment, the aforementioned formulation of the invention is taken at least twice a day. In yet a further embodiment, the aforementioned formulation of the invention is taken at least three times a day. In a further preferred embodiment, the formulation of the invention is taken at least four times a day. In a most preferred embodiment the formulation of the embodiment is taken orally four times a day.

The invention also comprises methods of alleviating or reducing pain in a subject by administering to said subject the above mentioned formulation.

In another aspect, the invention comprises a method of reducing pain in a subject with osteoarthritis in a joint by administering to the subject a pharmaceutical composition that modulates the level of a molecule present in the synovial fluid of said joint, wherein the molecule is selected from the group consisting of: Alpha-1-Antitrypsin (AAT); Alpha-2-Macroglobulin (A2Macro); Beta-2-Microglobulin (B2M); Brain-Derived Neurotrophic Factor (BDNF); C-Reactive Protein (CRP); Eotaxin-1; Factor VI; Ferritin (FRTN); Fibrinogen; Granulocyte-Macrophage Colony-Stimulat Factor (GM-CSF); Haptoglobin; Intercellular Adhesion Molecule 1 (ICAM-1); Interferon gamma (IFN-gamma); Interleukin-1 alpha (IL-1 alpha); Interleukin-1 beta (IL-1 beta); Interleukin-1 receptor antagonist (IL-1ra); Interleukin-2 (IL-2); Interleukin-3 (IL-3); Interleukin-4 (IL-4); Interleukin-5 (IL-5); Interleukin-6 (IL-6); Interleukin-7 (IL-7); Interleukin-8 (IL-8); Interleukin-10 (IL-10); Interleukin-12 Subunit p40 (IL-12p40); Interleukin-12 Subunit p70 (IL-12p70); Interleukin-15 (IL-15); Interleukin-17 (IL-17); Interleukin-18 (IL-18); Interleukin-23 (IL-23); Macrophage Inflammatory Protein-1 alpha (MIP-1 alpha); Macrophage Inflammatory Protein-1 beta (MIP-1 beta); Matrix Metalloproteinase-3 (MMP-3); Matrix Metalloproteinase-9 (MMP-9); Monocyte Chemotactic Protein 1 (MCP-1); Stem Cell Factor (SCF); T-Cell-Specific Protein RANTES (RANTES); Tissue Inhibitor of Metalloproteinases 1 (TIMP-1); Tumor Necrosis Factor alpha (TNF-alpha); Tumor Necrosis Factor beta (TNF-beta); Tumor necrosis factor receptor 2 (TNFR2);

Vascular Cell Adhesion Molecule-1 (VCAM-1); Vascular Endothelial Growth Factor (VEGF); Vitamin D-Bind Protein (VDBP); von Willebrand Factor (vWF); and Complement C3 (C3).

In a preferred embodiment, the molecule that is modulated in the synovium of a subject after administration of the composition of the invention, is selected from the group consisting of: Brain-Derived Neurotrophic Factor (BDNF); C-Reactive Protein (CRP); Factor VII; Haptoglobin; intercellular Adhesion Molecule 1 (ICAM-1); Interferon gamma (IFN-gamma); Interleukin-3 (IL-3); Interleukin-15 (IL-15); Interleukin-17 (IL-17); Interleukin-23 (IL-23); T-Cell-Specific Protein RANTES (RANTES); Tumor Necrosis Factor alpha (TNF-alpha); Tumor Necrosis Factor beta (TNF-beta); Tumor necrosis factor receptor 2 (TNFR2); Vascular Cell Adhesion Molecule-1 (VCAM-1); von Willebrand Factor (vWF); Complement C3 (C3). In a further embodiment, the selected molecule of the aforementioned method(s) is not modulated in the serum. In a further embodiment, the composition of the invention modulates any two or more of the aforementioned molecules in the synovium, in the alternative any three or more of the aforementioned molecules, alternatively any four or more of the aforementioned molecules, alternatively any five or more of the aforementioned molecules, alternatively six or more of the aforementioned molecules, alternatively seven or more of the aforementioned molecules, alternatively eight or more of the aforementioned molecules, alternatively nine or more of the aforementioned molecules, alternatively ten or more of the aforementioned molecules. In a further embodiment the composition of the invention modulates VCAM-1 and ICAM-1 in combination with one or more of the aforementioned molecules. In an even more preferred embodiment, the pharmaceutical composition reduces the level of VCAM-1 and ICAM-1 in the synovial fluid of said joint.

The invention further encompasses a formulation consisting of the following: *Boswellia* 100 mg; Vitamin C 1000 mg; Ginger 250 mg Turmeric 400 mg; Vitamin D3 600 IU and Rutin 100 mg either in a unit dose or multiple dosage formulation(s). In a preferred embodiment, said formulation is substantially free of omega-3 fatty acids.

It should be noted that preferably the novel formulations of the invention can be delivered in any form but are preferably formulated to be delivered orally.

In a further embodiment, the formulation(s) of the invention are administered to subjects with osteoarthritis to reduce pain and improve functioning. In a preferred embodiment, the subjects suffer from osteoarthritis of the knee.

In a further aspect, the invention comprises a method of reducing the levels of VCAM-1 and ICAM-1 in the synovial fluid of the joint of a subject by administering a natural formulation. In one embodiment the natural formulation comprises an effective amount of *Boswellia*, Vitamin C, Ginger, Turmeric, Vitamin D3 and Rutin. In a further embodiment, the subject suffers from osteoarthritis. In a preferred embodiment, serum levels of VCAM-1 and ICAM-1 are not significantly reduced.

In a further aspect of the invention a subject that is receiving the natural formulation of the invention is not also concurrently receiving either NSAIDS. In another aspect, the subject is not receiving omega-3 fatty acids. In another embodiment the subject is receiving neither NSAIDs nor omega-3 fatty acids concurrently with the formulation of the invention.

Pain relief can be measured in a number of different ways as would be known to one of ordinary skill in the art. Preferably pain relief is measured by a subject's self-report on the Visual Analog Scale. In one embodiment of the invention, a subject's pain is reduced at least one point, preferably at least two points and most preferably at least three points on the Visual Analog Scale after being administered the formulation of the invention for at least twelve weeks.

It should be noted that the above detailed description of the invention should not be deemed as limiting ad the invention is more fully described by the examples below.

DESCRIPTION OF THE FIGURES AND APPENDICES AND TABLES

FIG. 1 is a flow chart showing the study design and the patient participation in the study. Group A consists of subjects treated with the Product of the invention, Group B is a placebo treated group and Group C was treated with the same formulation as Group A with the addition of Omega-3 fatty acids.

FIG. 2 shows the change in synovial markers. FIG. 2 (A) shows the change (decrease/increase) in pro-inflammatory markers throughout the study (represented as percentage of total pro-inflammatory markers). A decrease represents lower levels at 12 weeks compared to baseline (negative value), while an increase represents higher levels at 12 weeks compared to baseline (positive value). FIG. 2(B) shows on a marker by marker basis that there was an obvious trend toward higher reduction rate in Group A; 19 markers (46.3%) which had a negative delta following treatment with the product (Group A), had a positive delta in the placebo group (group B).

FIG. 3 shows the behavior of three markers: VCAM-1; ICAM-1 and C3 across all there treatment groups.

Figure 4:
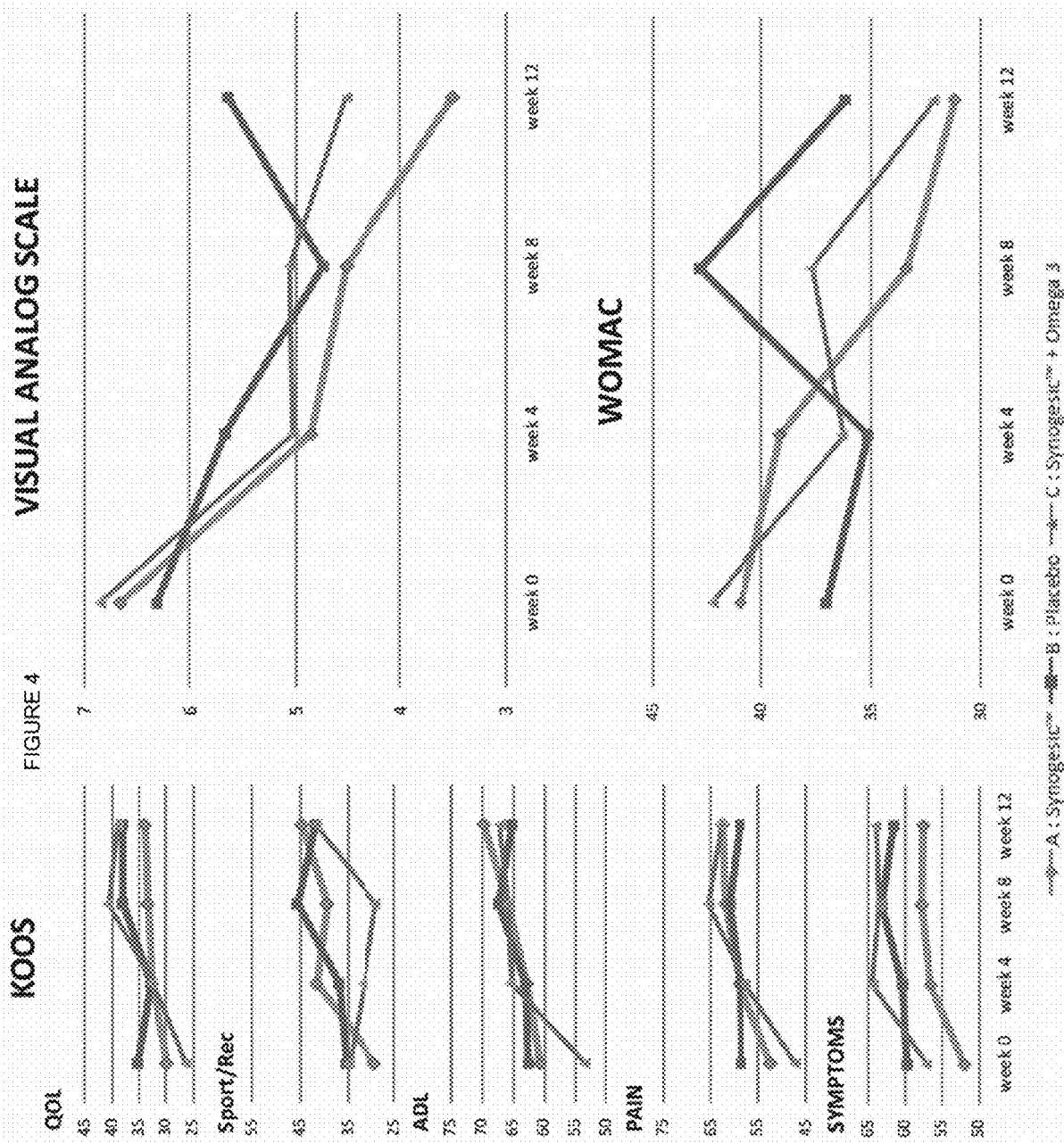
FIG. 4 is a depiction of the functional outcome and pain scores that were assessed in each time period throughout the study. Reduction in VAS scores in Group A were significant compared to Group C (P=0.05) at 12 weeks and compared to baseline (P=0.01).

Appendix A describes the subject inclusion/exclusion criteria.

Appendix B shows the difference in synovial fluid inflammatory markers between week 12 and baseline across all Groups.

Appendix C shows the difference in serum inflammatory markers between week 12 and baseline across all Groups.

Table 1 describes the demographics and baseline characteristics of the study groups.

Table 2 describes the functional outcomes and pain scores at different time periods.

EXAMPLES

Methods and Materials

A randomized, prospective, blinded study was conducted. Patients with symptomatic arthritis of the knee being defined as Kellegren-Lawrence grade II and III were allocated to one of three groups; treatment softgels (group A), placebo (Group B) or treatment softgels plus omega-3 (Group C). The treatment tablets contained *Boswellia* 100 mg. Vitamin C 1000 mg, Ginger 250 mg, Turmeric 400 mg, Vitamin D3 600 IU and Rutin 100 mg. Patients in the placebo group received identically appearing softgels that contained safflower oil only. The patients were seen at baseline and at weeks 4, 8 and 12 after enrollments. Various outcome measures were recorded in these patients, including numerous functional questionnaires, the Visual Analogue Scale (VAS) for pain and knee range of motion. Blood and synovial fluid samples were obtained from the patients at baseline and at the last follow-up and sent for measurement of various inflammatory markers. The primary outcome was the change in the level of inflammatory mediators in the serum and synovial fluid of patients who received the intervention versus placebo; Mean changes were compared using one-way analysis of variance (ANOVA). The secondary outcome measures were improvement in pain and function throughout time; Differences were compared between groups by repeated measures MANOVA.

The institutional review board approval was obtained and patients were approached to enroll in the study. Patients who signed the consent form were randomized using the block randomization technique to receive the treatment tablets (group A), placebo (Group B) or treatment tablets plus omega-3 (Group C). All patients were instructed to take the administered tablets four times a day. The treatment tablets contained Boswellia 100 mg, Vitamin C 1000 mg, Ginger 250 mg, Turmeric 400 mg, Vitamin D3 600 IU and Rutin 100 mg. Patients in the control group received identically appearing tablets that contained safflower oil only. Patients were given a diary to record the time at which the tablets were taken. During the period of the study patients were recommended to stop taking conventional NSAIDs, if possible, or record its use, if needed. Other simple analgesics, such as acetaminophen, were allowed. Consumption of opioid medications for control of symptoms of knee arthritis was also discouraged. Patients were asked to record the intake of any analgesics in addition to the tablets administered as part of the study. All other oral supplements for "treatment" of arthritis such as glucosamine were discontinued. During the period of study patients were not allowed to undergo intra-articular injection by any agents. Receiving such treatment resulted in disqualification of the patient for inclusion in the study. Patients unable to tolerate the study pills or those with low compliance were also excluded from the study.

Patient Selection

The study recruited 67 consecutive patients with a mean age of 62.9 years (range, 44.3 to 82.5 years) with symptomatic arthritis of the knee being defined as Kellegren-Lawrence grade II and III. There were 41 women and 26 men. Patients with systemic inflammatory conditions such as inflammatory bowel disease, psoriasis, eczema, or those with seropositive or seronegative inflammatory arthritis of the knee such as rheumatoid arthritis or ankylosing spondylitis were excluded. It was ensured that none of the patients had received intra-articular injection of any agents into the affected knee within 3 weeks prior to the enrollment (Appendix A summarizes inclusion and exclusion criteria).

Patient Assessment

The patients were seen at baseline (at the time of signing the consent form and enrollment to the study), week 4, 8 and 12 after enrollments. Various outcome measures were recorded in these patients. At the first visit, and enrollment, patients were assessed by the Lequesne's Functional Index score (LEQ) and a full clinical examination was performed. Knee range of motion was recorded. In addition a blood sample (5-7 ml) was obtained from the patients at baseline and the last follow-up. Aspiration of the joint was performed at baseline and also at the conclusion of the study to obtain between 3-5 ml of fluid (total of two serum and two synovial fluid samples). The aspiration of the knee was done under semi-sterile conditions in the office setting. If at first attempt inadequate amount of fluid was obtained or the tap was deemed to be dry, then a second attempt was made either during the same encounter (if the patient was willing) or a few days later. For patients with two dry taps, no further attempts at withdrawal of synovial fluid were made. The serum and synovial samples were stored at −30 C and sent in batched to Myriad RBM (Austin, Tex.) for measurement of various inflammatory markers (Appendix B and C).

Outcome Measures

The primary outcome was the change in the level of inflammatory mediators in the serum and synovial fluid of patients who received the intervention versus placebo. It was expected that those receiving the active agents would have a more significant drop in the level of inflammatory markers in both the serum and the synovial fluid compared to patients receiving the placebo. The secondary outcome measures included the following: range of motion of the knee (ROM) as recorded by a goniometer, Western Ontario and McMaster Universities Arthritis Index (WOMAC), Knee injury and Osteoarthritis Outcome Score (KOOS) and the Visual Analogue Scale (VAS) for pain.

Statistical Analysis:

Mean change in inflammatory markers between baseline and week 12 were compared using one-way analysis of variance (ANOVA). A post hoc analysis by using Bonferroni (Dunn) t test was performed for markers which showed a significant difference. Differences in subjective outcomes (WOMAC, KOOS, and VAS) and ROM were compared between groups at baseline, and weeks 4, 8 and 12 by repeated measures MANOVA. Wilks' Lambda test was used to assess significance between group differences at all times.

Results:

Of the 67 patients who met the inclusion criteria and agreed to take part in this study, 63 patients (22 in group A, 21 in group B and 20 in group C) completed the 12 week study period (FIG. 1). One patient from group C dropped off following an allergic reaction. Two patients from group B and one from group A were lost to follow-up. There were no differences in demographics and baseline characteristics between the 3 study groups (Table 1).

Change in Synovial Biomarkers:

Synovial samples at baseline and 12 weeks were available for 49 patients (Appendix B). Of the 41 pro-inflammatory markers examined, 25 (61%) decreased in group A, while only 13 (32%) and 9 (22%) decreased in group B and C respectively (FIG. 2). There were significant between group differences in the synovial levels of: Intercellular Adhesion Molecule 1 (ICAM-1), Vascular Cell Adhesion Molecule-1 (VCAM-1) and Complement C3 (C3) (P=0.03, 0.02, 0.04 respectively) (FIG. 3). A post hoc analysis revealed the significant difference in ICAM-1 was between group C and A (mean change 15.3, CI 0.95-29.65), while the differences in VCAM-1 and C3 were between group B and A (mean change 136.7; CI 7.1-266.3 and 0.26; CI 0.01-0.52, respectively). There were no significant differences between groups in the change in anti-inflammatory markers.

Change in Serum Biomarkers:

Serum samples at baseline and 12 weeks were available for 53 patients (Appendix C). Of the 41 pro-inflammatory markers examined, 22 (53.7%) decreased in group A, 15 (36.6%) decreased in group B and 21 (51.2%) decreased in C. There were no significant differences in serum biomarker levels between groups. ICAM-1 levels which were significantly reduced in the synovial fluid of group A were also reduced in their serum (delta −12.9) compared to group B (delta +19.3), without reaching significance (p=0.08)

Functional Outcomes and Pain Scores:

Table 2 and FIG. 4 summarize the functional outcomes and pain scores for the 3 groups throughout the study. Between group comparisons throughout time indicated VAS scores were significantly better in group A compared to group B at 12 weeks (P=0.05). There was also a significant decrease in VAS score in group A at 12 weeks compared to baseline (P=0.01), but not for groups B and C. The VAS scores improved at 12 weeks by 3.2 points (48.5%) in group A compared to 2.3 points (36.5%) in group C and 0.6 points (8.8%) in group B. While WOMAC and KOOS scores improved in all groups at 12 weeks compared to baseline, especially in the treatment groups (A and C) compared to placebo, there were no significant differences between groups throughout the study. Notably, KOOS scores for pain improved by 10.3 and 15.6 points in groups A and C compared to only 0.2 points in group B by the end of the study. Range of motion was similar between patients throughout the study.

Adverse Outcomes and Pain Management:

One patient in group C suffered from hives 4 weeks into the study. The reaction was considered of moderate severity. There were no additional adverse outcomes associated with treatment. The data regarding intake of analgesics throughout the study was only partial. One patient from group A was taking NSAIDS at baseline and stopped them completely by the end of the study. One patient from group C was taking NSAIDS at baseline and continued the treatment throughout the study. One patient from group B started taking NSAIDS 8 weeks into the study. No additional analgesic treatment was documented.

Discussion

A total of 63 patients (22 in group A, 21 in group B and 20 in group C) completed the study. There was a significant between group difference in the synovial levels of: Intercellular Adhesion Molecule 1 (ICAM-1), Vascular Cell Adhesion Molecule-1 (VCAM-1) and Complement C3 (C3) (P=0.03, 0.02, 0.04 respectively). Of the 41 pro-inflammatory markers examined in the synovial fluid, 25 (61%) decreased in group A, while only 13 (32%) and 9 (22%) decreased in group B and C respectively. The reduction in inflammatory markers correlated to pain relief; VAS scores significantly decreased in group A (48.5%) compared to baseline (P=0.01) and compared to group B (8.8%) (P=0.05). There was no significant difference in the change in serum biomarker levels between groups.

Our study shows the effectiveness of natural anti-inflammatories in reducing intra-articular inflammatory markers in patients with moderate knee osteoarthritis. These agents helped in alleviating pain as well. Our findings suggest that intra-articular reduction in inflammatory mediators is responsible for the clinical benefit demonstrated by these agents. Certain agents, when taken together may decrease potency and should be avoided.

Naturally occurring anti-inflammatory agents through their broad mechanism of action inhibit both lipoxygenase and cyclooxygenase pathways, as well as the complement system. They also directly inhibit metalloproteinase and cartilage destruction. Products such as *Boswellia*, Turmeric, Vitamin C and Ginger have shown in-vitro to reduce inflammatory markers. Our findings support these anti-inflammatory properties in human synovial fluid; more than 60% of the pro-inflammatory markers examined showed a decrease in levels following treatment. Moreover, VCAM and ICAM, which have been shown to play an important role in endothelial-leukocyte interactions during inflammation and have been a target for treatment in patients with OA, were significantly affected by natural anti-inflammatories in the present study.

Few studies examined the effect of these agents on serum inflammatory markers in humans. They show a decrease in pro-inflammatory cytokines following treatment. However, these studies were conducted on patients with a systemic pro-inflammatory state. In patients with lower levels of systemic inflammation such as OA, this effect seems to be less obvious. Rahimnia et al. examined the effect of curcuminoids on serum levels of IL-4, IL-6, TNF-α, TGF-β and high-sensitivity (hs) CRP and ESR in mild to moderate knee osteoarthritis. They reported a reduction in IL-4, IL-6 and hs-CRP levels at 6 weeks compared to baseline, but there were no significant differences compared to placebo (p>0.05). While we demonstrate a significant reduction in synovial markers between groups, the reduction in serum markers was not significant. These results suggest the local effect of these products might outweigh their systematic effect and be responsible to the clinical improvement seen in osteoarthritic patients. Similar to Rahimnia and colleges, natural anti-inflammatories in our study did not elevate levels of anti-inflammatory markers (IL-10, IL-4) in the serum or synovial fluid. Thus, the decrease in pro-inflammatory markers cannot be explained by a mechanism based on the suppression by these cytokines, and other explanation is needed.

Earlier randomized control trials focus mainly on clinical and functional improvement of these agents with promising results. We strengthen these studies by showing that natural anti-inflammatories reduce pain; in the present study there was a 48.5% reduction in pain levels based on the VAS score. Whereas earlier studies suggest this improvement is secondary to reduced cytokine levels, they base their assumption mainly on in-vitro models. Our study confirms these experimental observations in humans and correlates them with clinical outcomes. Omega 3 is a potent anti-inflammatory which has shown beneficial effect in OA. We hypothesized it could add to the efficacy of the product in the group of patients receiving dual therapy. Surprisingly, not only it did not improve results, but it even demonstrated an inhibitory effect when added to the product. A mixture of agents working on the same enzyme could produce unexpected consequences and result in pharmacokinetic or pharmacodynamic interactions, or a combination of both. A possible explanation for the antagonistic interaction seen in this study could be secondary to the non-competitive nature of *Boswellia*, a potent agent in the product. This could lead to minor structural changes in common pathways such as 5-lipoxygenase (5-LOX) and NF-kappa B and possibly alternating their affinity to omega 3.

The main limitation of the present study is the limited number of patients in each group. There were also a substantial number of patients in the cohort for whom serum and synovial markers were not available due to dry tap or human error. This probably contributed to the lack of significance in some of parameters evaluated. Nevertheless, only few patients dropped off and the number of patients analyzed was sufficient to show significant clinical and laboratory improvement. Another limitation was that the product included several anti-inflammatory agents working through different mechanisms. Thus it is hard to distinguish the relative effect of each agent on the outcomes or their possible interactions with omega-3. Finally, we followed the patients for 12 weeks and we cannot tell whether the improvement in pain and inflammatory markers continues with long term treatment. Future studies should focus on the long term effect of these agents and the potential interactions with other agents.

CONCLUSION

Natural anti-inflammatory agents hold a great promise in the management of patients with arthritis as they may reduce inflammation while avoiding the sometimes serious adverse effects of synthetic drugs. These agents have been shown in this study to reduce intra-articular inflammatory mediatorand pain levels. This takes us one step closer to understanding the efficacy of these agents in knee osteoarthritis.

TABLE 1

Demographics and baseline characteristics of the study group.

| Characteristic | Group A (n = 22) | Group B (n = 21) | Group C (n = 20) | p-value |
|---|---|---|---|---|
| Age | 64.1 ± 8.6 | 61.2 ± 6.6 | 63.1 ± 7.6 | 0.455(ANOVA) |
| Sex | | | | |
| Male | 10 (45.5%) | 9 (42.9%) | 6 (30%) | 0.587(fisher's exact) |
| Female | 12 (54.5%) | 12 (57.1%) | 14 (70%) | |
| Race | | | | |
| White | 20 (90.9%) | 21 (100%) | 17 (85.0%) | 0.172 (fisher's exact) |
| Black | 0 (0%) | 0 (0%) | 2 (10.0%) | |
| Other | 2 (9.1%) | 0 (0%) | 1 (5.0%) | |
| ROM | 120.7 ± 12.4 | 118.5 ± 11.9 | 117.3 ± 11.0 | 0.532(ANOVA) |
| LEQ score | 11.0 ± 2.6 | 11.4 ± 3.2 | 12.1 ± 3.6 | 0.470(ANOVA) |
| VAS score | 6.6 ± 2.5 | 6.3 ± 2.3 | 6.8 ± 2.3 | 0.848(ANOVA) |
| WOMAC score | 40.9 ± 17.3 | 37.0 ± 16.1 | 42.2 ± 22.6 | 0.662(ANOVA) |
| KOOS | | | | |
| Symptoms | 51.8 ± 51.8 | 59.7 ± 17.8 | 57.1 ± 14.1 | 0.317(ANOVA) |
| Pain | 52.3 ± 16.8 | 58.5 ± 16.2 | 47.2 ± 19.3 | 0.166(ANOVA) |
| ADL | 60.7 ± 19.3 | 62.5 ± 15.5 | 53.5 ± 19.9 | 0.226(ANOVA) |
| Sport/Rec | 29.0 ± 26.1 | 35.2 ± 27.3 | 34.6 ± 26.9 | 0.572(ANOVA) |
| QOL | 29.8 ± 23.5 | 35.1 ± 16.9 | 26.3 ± 19.3 | 0.395(ANOVA) |

Data is presented as mean (SD) or number (%)
Lequesne's Functional Index score (LEQ); Range of motion (ROM); Function in daily living (ADL); Function in sport and recreation (Sport/Rec); Knee related Quality of life (QOL); Western Ontario and McMaster Universities Arthritis Index (WOMAC); Knee injury and Osteoarthritis Outcome Score (KOOS).

TABLE 2

Functional outcomes and pain scores at different time periods.

| | | | week 0 | week 4 | week 8 | week 12 | Pr > F° |
|---|---|---|---|---|---|---|---|
| VAS | | Group A | 6.67 | 4.86 | 4.52 | 3.50 | 0.03 |
| | | Group B | 6.31 | 5.67 | 4.75 | 5.64 | |
| | | Group C | 6.84 | 5.03 | 5.05 | 4.53 | |
| KOOS | QOL | Group A | 29.79 | 32.56 | 33.24 | 33.81 | 0.45 |
| | | Group B | 35.13 | 32.81 | 37.97 | 37.97 | |
| | | Group C | 26.31 | 32.50 | 40.63 | 38.88 | |
| | Sport/Rec | Group A | 29.00 | 41.53 | 39.31 | 44.50 | 0.23 |
| | | Group B | 35.18 | 36.91 | 45.60 | 41.79 | |
| | | Group C | 34.63 | 31.62 | 28.91 | 41.51 | |
| | ADL | Group A | 60.70 | 62.66 | 65.87 | 69.72 | 0.21 |
| | | Group B | 62.51 | 62.94 | 67.28 | 65.04 | |
| | | Group C | 53.47 | 65.28 | 65.80 | 67.14 | |
| | Pain | Group A | 52.27 | 58.89 | 62.11 | 62.63 | 0.21 |
| | | Group B | 58.48 | 58.73 | 61.11 | 58.73 | |
| | | Group C | 47.22 | 57.70 | 65.50 | 62.87 | |
| | Symptoms | Group A | 51.82 | 56.49 | 57.79 | 57.63 | 0.72 |
| | | Group B | 59.69 | 60.38 | 63.27 | 61.66 | |
| | | Group C | 57.10 | 64.42 | 63.39 | 63.93 | |
| WOMAC | | Group A | 40.92 | 39.14 | 33.38 | 31.15 | 0.34 |
| | | Group B | 37.05 | 35.17 | 42.85 | 36.16 | |
| | | Group C | 42.24 | 36.26 | 37.68 | 32.13 | |
| ROM | | Group A | 120.67 | 117.78 | 118.61 | 119.44 | 0.74 |
| | | Group B | 118.53 | 117.65 | 116.47 | 118.53 | |
| | | Group C | 117.35 | 115.18 | 115.00 | 118.94 | |

Range of motion (ROM); Function in daily living (ADL); Function in sport and recreation (Sport/Rec); Knee related Quality of life (QOL); Visual Analog Scale (VAS); Western Ontario and McMaster Universities Arthritis Index (WOMAC); Knee injury and Osteoarthritis Outcome Score (KOOS).
°Wilks' Lambda test was used to assess significance between group differences at all times.

APPENDIX A: SUBJECT SELECTION CRITERIA

Inclusion Criteria:
1. Age ≥18 and ≤90 at the time of informed consent.
2. Subjects with symptomatic moderate arthritis of the knee defined as per Kellgren-Lawrence grade II or III.
3. In subjects with bilateral arthritis of the knee, only one knee will be enrolled into the study.
4. Ability to walk 50 feet unassisted.
5. Lequesne's Functional Index score greater than 7 points.
6. Must understand; be willing and able, and likely to fully comply with study procedures, visit schedule, and restrictions.

Exclusion Criteria:
1. Subjects with systemic inflammatory conditions such as inflammatory bowel disease, psoriasis, eczema, and others 2. Subjects with seropositive or sero-negative inflammatory arthritis of the knee such as rheumatoid arthritis or ankylosing spondylitis.
3. Subjects taking hormone replacement therapy
4. Intra-articular corticosteroid injections 3 weeks prior to enrollment.
5. Hypersensitivity to fish oil.
6. Hypersensitivity to non-steroidal anti-inflammatory drugs, abnormal liver of kidney function tests, history of peptic ulceration and upper gastrointestinal hemorrhage, congestive heart failure, Hypertension (BP>140/90), cancer and hyperkalemia.
7. Major abnormal findings on complete blood count, history of coagulopathies, hematological or neurological disorders.
8. High alcohol intake (≥2 standard drinks per day).
9. Pregnant, breastfeeding or planning to become pregnant during the study
10. Subjects awaiting surgery on the affected knee within three months.

APPENDIX B

Difference in synovial fluid inflammatory markers between week 12 and baseline.

| Synovial Fluid Markers | A Week 12-Baseline | SD | B Week 12-Baseline | SD | C Week 12 Baseline | SD | Pr > F |
|---|---|---|---|---|---|---|---|
| Alpha-1-Antitrypsin (AAT) | −0.1611 | 0.3436 | 0.0647 | 0.3390 | 0.1038 | 0.4824 | 0.1 |
| Alpha-2-Macroglobulin (A2Macro) | −0.1418 | 0.2642 | 0.0779 | 0.3609 | 0.0849 | 0.3939 | 0.2 |
| Beta-2-Microglobulin (B2M) | −0.2606 | 0.5659 | −0.0707 | 0.5832 | 0.0093 | 0.5735 | 0.4 |
| Brain-Derived Neurotrophic Factor (BDNF) | −1.0883 | 3.7283 | 1.8777 | 7.2110 | 1.6984 | 6.4026 | 0.3 |
| C-Reactive Protein (CRP) | −1.7366 | 6.2976 | 0.3190 | 1.0077 | −0.3736 | 0.8620 | 0.3 |
| Eotaxin-1 | 8.4444 | 19.9181 | 4.6000 | 17.1789 | 24.3571 | 85.7085 | 0.5 |
| Factor VII | −3.5000 | 27.7515 | 17.0000 | 43.1807 | 32.1929 | 93.0848 | 0.2 |
| Ferritin (FRTN) | 47.6111 | 1348.9668 | 26.0667 | 102.6384 | 49.3571 | 109.8283 | 1 |
| Fibrinogen | −0.0273 | 0.0616 | −0.0008 | 0.0443 | −0.0106 | 0.0585 | 0.4 |
| Granulocyte-Macrophage Colony-Stimulat Factor (GM-CSF) | 0.7778 | 3.2998 | −0.9333 | 3.6148 | −1.0000 | 3.7417 | 0.3 |
| Haptoglobin | −0.1448 | 0.4082 | 0.0667 | 0.3504 | 0.0855 | 0.7088 | 0.3 |
| Intercellular Adhesion Molecule 1 (ICAM-1) | −5.4722 | 10.3763 | 4.4533 | 11.2480 | 9.8286 | 24.6707 | 0.03 |
| Interferon gamma (IFN-gamma) | −0.1000 | 0.4243 | 0.1200 | 0.4648 | 0.1286 | 0.4811 | 0.3 |
| Interleukin-1 alpha (IL-1 alpha) | 0.0000 | 0.0000 | −0.0001 | 0.0003 | 0.0000 | 0.0001 | 0.2 |
| Interleukin-1 beta (IL-1 beta) | 0.0333 | 0.7608 | 0.1533 | 0.4941 | 0.5357 | 1.4882 | 0.3 |
| Interleukin-1 receptor antagonist (IL-1ra) | 258.6667 | 1198.6569 | 4.0000 | 11.7534 | 12.5000 | 36.1658 | 0.5 |
| Interleukin-2 (IL-2) | 0.6667 | 2.8284 | −0.8000 | 3.0984 | −0.8571 | 3.2071 | 0.3 |
| Interleukin-3 (IL-3) | −0.0001 | 0.0005 | 0.0002 | 0.0006 | 0.0002 | 0.0006 | 0.3 |
| Interleukin-4 (IL-4) | −2.1667 | 5.3072 | 2.6000 | 5.8138 | 3.2500 | 6.5000 | 0.3 |
| Interleukin-5 (IL-5) | −0.0667 | 0.2828 | 0.0800 | 0.3098 | 0.0857 | 0.3207 | 0.3 |
| Interleukin-6 (IL-6) | −8.2444 | 58.5871 | −54.7533 | 199.5999 | −22.6143 | 53.2886 | 0.5 |
| Interleukin-7 (IL-7) | −1.1667 | 4.9497 | 1.4000 | 5.4222 | 1.5000 | 5.6125 | 0.3 |
| Interleukin-8 (IL-8) | 102.2222 | 421.5444 | 71.9867 | 194.9395 | 539.3714 | 2045.3196 | 0.5 |
| Interleukin-10 (IL-10) | −0.1500 | 0.7702 | 0.2467 | 0.8271 | 0.5429 | 1.5286 | 0.2 |
| Interleukin-12 Subunit p40 (IL-12p40) | 0.0222 | 0.0713 | 0.0200 | 0.0656 | 0.0207 | 0.1652 | 1 |
| Interleukin-12 Subunit p70 (IL-12p70) | 0.7222 | 3.0641 | −0.8667 | 3.3566 | −0.9286 | 3.4744 | 0.3 |
| Interleukin-15 (IL-15) | −0.0428 | 0.1899 | 0.0600 | 0.1970 | 0.0593 | 0.2205 | 0.2 |
| Interleukin-17 (IL-17) | −0.3333 | 1.4142 | 0.4200 | 1.5456 | 0.4714 | 1.5992 | 0.2 |
| Interleukin-18 (IL-18) | −67.3889 | 137.8930 | −12.0667 | 60.7659 | −68.7143 | 329.5534 | 0.7 |
| Interleukin-23 (IL-23) | −0.1111 | 0.6057 | 0.2200 | 0.6732 | 0.2571 | 1.0390 | 0.3 |
| Macrophage Inflammatory Protein-1 alpha (MIP-1 alpha) | 1.1667 | 12.9263 | 1.8667 | 5.4231 | 14.4286 | 40.6575 | 0.2 |
| Macrophage Inflammatory Protein-1 beta (MIP-1 beta) | 10.5000 | 197.5146 | −19.6000 | 128.3638 | 55.7857 | 180.7651 | 0.5 |
| Matrix Metalloproteinase-3 (MMP-3) | 3.9000 | 21.2785 | −12.2267 | 23.7722 | 1.2286 | 17.4736 | 0.08 |
| Matrix Metalloproteinase-9 (MMP-9) | −26.8889 | 80.5875 | −0.6667 | 2.3197 | 0.2143 | 4.0226 | 0.2 |
| Monocyte Chemotactic Protein 1 (MCP-1) | 400.1111 | 1649.9386 | −49.1333 | 237.2768 | 18.0714 | 250.4545 | 0.4 |
| Stem Cell Factor (SCF) | 28.7222 | 99.1557 | 38.3333 | 84.8736 | 60.3571 | 213.1286 | 0.8 |
| T-Cell-Specific Protein RANTES (RANTES) | −1.9759 | 6.1013 | 1.8180 | 6.9367 | 1.1180 | 3.4925 | 0.1 |
| Tissue Inhibitor of Metalloproteinases 1 (TIMP-1) | 38.1111 | 225.1067 | 54.2667 | 140.1191 | 8.0714 | 141.9103 | 0.7 |
| Tumor Necrosis Factor alpha (TNF-alpha) | −0.5000 | 2.1213 | 0.6000 | 2.3238 | 0.6429 | 2.4054 | 0.3 |
| Tumor Necrosis Factor beta (TNF-beta) | −2.6111 | 11.0780 | 3.1333 | 12.1353 | 3.3571 | 12.5613 | 0.3 |
| Tumor necrosis factor receptor 2 (TNFR2) | −0.8444 | 1.7236 | 0.3867 | 1.3147 | 0.7357 | 2.6008 | 0.06 |
| Vascular Cell Adhesion Molecule-1 (VCAM-1) | −49.9444 | 198.9846 | 86.8000 | 125.7788 | 76.8571 | 79.2152 | 0.02 |
| Vascular Endothelial Growth Factor (VEGF) | 539.2222 | 1298.7280 | 140.0667 | 379.8905 | 190.6429 | 445.4572 | 0.4 |
| Vitamin D-Bind Protein (VDBP) | −46.0526 | 84.3626 | −30.5333 | 147.6665 | −4.6429 | 125.7578 | 0.6 |
| von Willebrand Factor (vWF) | −4.4444 | 17.8728 | 3.5333 | 13.4104 | 10.3571 | 27.8943 | 0.1 |
| Complement C3 (C3) | −0.2120 | 0.2974 | 0.0567 | 0.3087 | −0.0911 | 0.2541 | 0.04 |

APPENDIX C

Difference in serum inflammatory markers between week 12 and baseline.

| Serum Marker | A | | B | | C | | |
| --- | --- | --- | --- | --- | --- | --- | --- |
| | Week 12-Baseline | SD | Week 12-Baseline | SD | Week 12-Baseline | SD | Pr > F |
| Alpha-1-Antitrypsin (AAT) | 0.032 | 0.600 | 0.057 | 0.718 | -0.190 | 0.656 | 0.5 |
| Alpha-2-Macroglobulin (A2Macro) | -0.328 | 1.375 | -0.128 | 1.055 | -0.653 | 1.196 | 0.5 |
| Beta-2-Microglobulin (B2M) | 0.035 | 0.665 | 0.018 | 0.397 | -0.183 | 0.479 | 0.4 |
| Brain-Derived Neurotrophic Factor (BDNF) | 1.295 | 9.167 | -0.419 | 6.429 | -3.229 | 5.910 | 0.2 |
| C-Reactive Protein (CRP) | -14.722 | 60.383 | 2.698 | 4.567 | -2.519 | 5.621 | 0.3 |
| Eotaxin-1 | -0.200 | 140.018 | 23.000 | 224.341 | -17.000 | 225.108 | 0.8 |
| Factor VII | -8.000 | 190.173 | -13.111 | 211.038 | -49.067 | 164.963 | 0.8 |
| Ferritin (FRTN) | -1.900 | 107.548 | -10.556 | 109.113 | -10.267 | 86.711 | 0.9 |
| Fibrinogen | 0.000 | 0.000 | -0.069 | 0.297 | -0.001 | 0.003 | 0.4 |
| Granulocyte-Macrophage Colony-Stimulating Factor (GM-CSF) | -0.700 | 3.130 | 3.556 | 18.627 | 17.533 | 75.811 | 0.4 |
| Haptoglobin | -0.244 | 1.040 | -0.040 | 0.891 | -0.366 | 1.042 | 0.6 |
| Intercellular Adhesion Molecule 1 (ICAM-1) | -12.950 | 43.872 | 19.333 | 47.209 | 4.473 | 36.712 | 0.08 |
| Interferon gamma (IFN-gamma) | 0.090 | 0.402 | 0.444 | 1.498 | 0.240 | 0.633 | 0.5 |
| Interleukin-1 alpha (IL-1 alpha) | 0.000 | 0.000 | 0.003 | 0.011 | 0.000 | 0.000 | 0.3 |
| Interleukin-1 beta (IL-1 beta) | -0.500 | 2.070 | 328.933 | 165.003 | 22.473 | 90.776 | 0.3 |
| Interleukin-1 receptor antagonist (IL-1ra) | 43.950 | 219.417 | 144.611 | 779.955 | -12.800 | 595.078 | 0.7 |
| Interleukin-2 (IL-2) | -0.600 | 2.683 | 1.556 | 8.046 | -1.600 | 4.222 | 0.2 |
| Interleukin-3 (IL-3) | 0.000 | 0.001 | 0.001 | 0.002 | 0.000 | 0.001 | 0.5 |
| Interleukin-4 (IL-4) | 2.167 | 5.307 | 1.625 | 4.596 | 4.333 | 6.713 | 0.6 |
| Interleukin-5 (IL-5) | 0.060 | 0.268 | 0.067 | 0.283 | 0.160 | 0.422 | 0.6 |
| Interleukin-6 (IL-6) | -0.610 | 3.842 | 614.533 | 1954.243 | 98.473 | 381.255 | 0.2 |
| Interleukin-7 (IL-7) | 1.050 | 4.696 | 1.611 | 5.192 | 2.800 | 7.389 | 0.7 |
| Interleukin-8 (IL-8) | 200.745 | 582.611 | 1344.306 | 2940.668 | 900.413 | 2377.799 | 0.3 |
| Interleukin-10 (IL-10) | 0.080 | 0.483 | 0.656 | 2.425 | 0.247 | 1.436 | 0.5 |
| Interleukin-12 Subunit p40 (IL-12p40) | -0.053 | 0.178 | -0.047 | 0.363 | -0.091 | 0.219 | 0.9 |
| Interleukin-12 Subunit p70 (IL-12p70) | -0.650 | 2.907 | -0.722 | 3.064 | -1.733 | 4.574 | 0.6 |
| Interleukin-15 (IL-15) | -0.013 | 0.216 | -0.017 | 0.205 | 0.027 | 0.240 | 0.8 |
| Interleukin-17 (IL-17) | 0.130 | 1.012 | 0.394 | 1.193 | 0.573 | 1.655 | 0.6 |
| Interleukin-18 (IL-18) | 63.550 | 280.554 | -34.167 | 346.874 | -114.400 | 350.997 | 0.3 |
| Interleukin-23 (IL-23) | -0.263 | 0.632 | -0.356 | 1.023 | -0.320 | 0.937 | 0.9 |
| Macrophage Inflammatory Protein-1 alpha (MIP-1 alpha) | 3.300 | 18.070 | 2077.167 | 7745.00 | 391.000 | 1494.645 | 0.3 |
| Macrophage Inflammatory Protein-1 beta (MIP-1 beta) | 71.000 | 218.275 | 2540.611 | 8519.91 | 369.667 | 1658.790 | 0.3 |
| Matrix Metalloproteinase-3 (MMP-3) | -1.825 | 6.551 | -0.111 | 5.700 | -0.060 | 20.846 | 0.9 |
| Matrix Metalloproteinase-9 (MMP-9) | -5.550 | 13.117 | -4.667 | 15.204 | -14.000 | 35.080 | 0.4 |
| Monocyte Chemotactic Protein 1 (MCP-1) | 35.450 | 199.774 | 845.056 | 2205.61 | 1020.333 | 4237.373 | 0.5 |
| Stem Cell Factor (SCF) | 39.450 | 163.306 | 52.444 | 141.956 | 58.200 | 164.964 | 0.9 |
| T-Cell-Specific Protein RANTES (RANTES) | 0.295 | 7.812 | -3.873 | 14.366 | -3.930 | 17.052 | 0.5 |
| Tissue Inhibitor of Metalloproteinases 1 (TIMP-1) | -0.400 | 21.886 | 13.056 | 43.387 | 1.600 | 33.936 | 0.4 |
| Tumor Necrosis Factor alpha (TNF-alpha) | 0.400 | 2.037 | 66.056 | 263.734 | 5.667 | 19.134 | 0.4 |
| Tumor Necrosis Factor beta (TNF-beta) | 2.350 | 10.510 | 2.833 | 11.063 | 6.267 | 16.538 | 0.6 |
| Tumor necrosis factor receptor 2 (TNFR2) | 0.640 | 2.672 | 0.394 | 3.266 | 0.107 | 3.295 | 0.9 |
| Vascular Cell Adhesion Molecule-1 (VCAM-1) | 34.350 | 224.024 | 36.833 | 230.255 | -33.733 | 185.989 | 0.6 |
| Vascular Endothelial Growth Factor (VEGF) | -23.700 | 214.683 | 199.056 | 472.956 | 22.600 | 230.977 | 0.1 |
| Vitamin D-Binding Protein (VDBP) | -12.300 | 95.742 | -21.889 | 80.744 | -50.000 | 71.777 | 0.4 |
| von Willebrand Factor (vWF) | -31.600 | 53.645 | 4.333 | 63.105 | -12.933 | 60.358 | 0.2 |
| Complement C3 (C3) | -0.326 | 0.356 | -0.041 | 0.608 | -0.358 | 0.334 | 0.1 |

What is claimed is:

1. A tablet consisting essentially of *Boswellia*, Vitamin C, Ginger, Tumeric, Vitamin D3 and Rutin, in a ratio of 2:20:5:8:12:2, respectively.

* * * * *